United States Patent [19]

Lee et al.

[11] Patent Number: 5,613,972
[45] Date of Patent: Mar. 25, 1997

[54] SURGICAL CUTTING HEADS WITH CURLED CUTTING WINGS

[75] Inventors: William Lee; Izuru Nose; Jean-Marie Parel, all of Miami, Fla.

[73] Assignee: The University of Miami, Miami, Fla.

[21] Appl. No.: 304,843

[22] Filed: Sep. 13, 1994

Related U.S. Application Data

[63] Continuation-in-part of Ser. No. 111,591, Aug. 25, 1993, Pat. No. 5,346,497, which is a continuation of Ser. No. 913,474, Jul. 15, 1992, abandoned.

[51] Int. Cl.$^6$ ............... A61F 9/00; A61B 17/00
[52] U.S. Cl. ............... 606/107; 606/80; 606/180
[58] Field of Search ................ 606/1, 79, 80, 606/107, 159, 166–172, 176–180; 408/204; 604/19, 21, 35

[56] References Cited

U.S. PATENT DOCUMENTS

| | | |
|---|---|---|
| 2,492,158 | 12/1949 | Le Compte . |
| 3,732,858 | 5/1973 | Banko . |
| 3,776,238 | 12/1973 | Peyman . |
| 3,815,604 | 6/1974 | O'Malley . |
| 3,882,872 | 5/1975 | Douvas . |
| 3,976,077 | 8/1976 | Kerfoot . |
| 3,990,453 | 11/1976 | Douvas ............... 606/107 |
| 3,996,935 | 12/1976 | Banko . |
| 4,014,342 | 3/1977 | Staub . |
| 4,167,944 | 9/1979 | Banko . |
| 4,320,761 | 3/1982 | Haddad . |
| 4,368,734 | 1/1983 | Banko . |
| 4,530,356 | 7/1985 | Helfgott . |
| 4,531,934 | 7/1985 | Kossovsky . |
| 4,634,420 | 1/1987 | Spinosa . |
| 4,649,918 | 3/1987 | Pegg . |
| 4,649,919 | 3/1987 | Thimsen . |
| 4,689,040 | 8/1987 | Thompson ............... 604/22 |
| 4,706,669 | 11/1987 | Schlegel . |
| 4,782,833 | 11/1988 | Einhorn . |
| 4,785,826 | 11/1988 | Ward . |
| 4,825,865 | 5/1989 | Zelman . |
| 4,869,716 | 8/1989 | Smirmaul . |
| 4,909,249 | 3/1990 | Akkas . |
| 4,986,827 | 1/1991 | Akkas . |
| 5,112,299 | 5/1992 | Pascaloff . |
| 5,423,330 | 6/1995 | Lee ............... 606/166 |

FOREIGN PATENT DOCUMENTS

| | | |
|---|---|---|
| 0439281 | 1/1975 | U.S.S.R. . |
| 0984770 | 1/1983 | U.S.S.R. . |

*Primary Examiner*—Glenn Dawson
*Attorney, Agent, or Firm*—Cushman Darby & Cushman IP Group of Pillsbury Madison & Sutro LLP

[57] ABSTRACT

A surgical cutting head includes an outer tube rotatably housing an inner tube. At the distal end of the inner tube is curled cutting wings characterized by a portion of the wall of the inner tube being radially displaced inwardly. The distal end of the inner tube also has v-shaped cutting notches. The distal end of the outer tube has a projecting guard having a poriton which overlies the cutting wings and the distal edge of the inner tube.

18 Claims, 3 Drawing Sheets

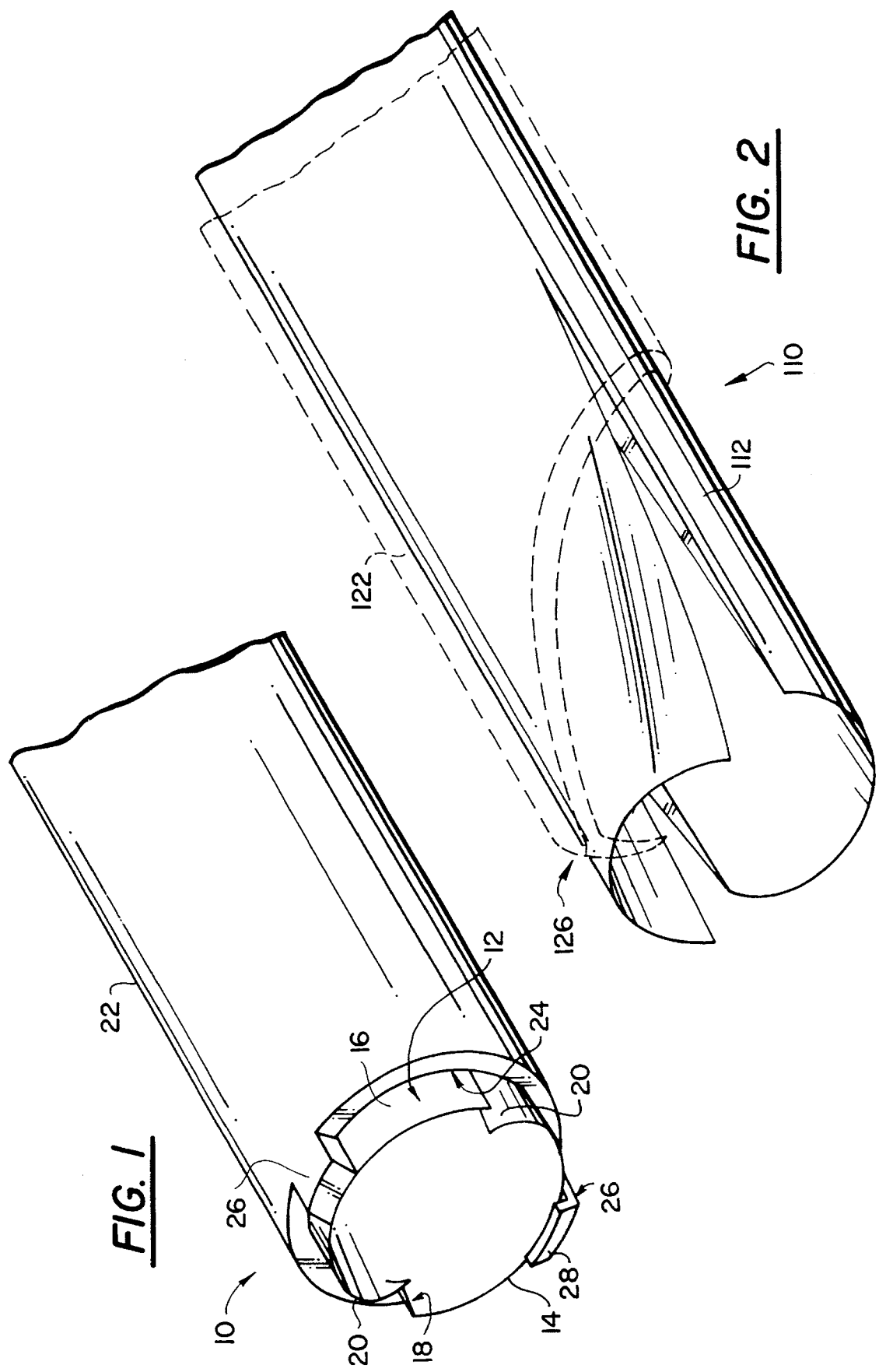

SURGICAL CUTTING HEADS WITH CURLED CUTTING WINGS

This is a continuation-in-part of our prior application Ser. No. 08/111,591, filed Aug. 25, 1993, now U.S. Pat. No. 5,346,497, which was a continuation of application Ser. No. 07/913,474, filed Jul. 15, 1992, and now abandoned.

BACKGROUND OF THE INVENTION

1. Field of the Invention

This invention relates to surgical cutting instruments. More particularly, this invention relates to novel surgical cutting heads or tips for performing surgery on various parts of the body, such as menisci (fibrous cartilages) located in body joints, e.g., knees, elbows and shoulders, or to remove malignant or non-malignant fibroids or similar tissues through small incisions in various parts of the body, and especially for use in infusion/aspiration devices for surgically removing cataractous tissue from the eye. The surgical cutting instruments of this invention will be described herein with reference in particular to cataract surgery.

2. Description of the Related Art

The eye's lens, a tough, almost completely transparent biconvex structure suspended behind the iris, is made up of an elastic capsule filled with cellular tissue. The lens is susceptible to cataract formation—changes in the lens which make it opaque and which may hinder or destroy vision depending on the size, shape and location of the cataract. Cataracts can be congenital. They can also be caused by degenerative changes in the lens with age (senile cataracts). Cataracts can also result from trauma, or from overexposure of the eye to heat, X-rays, ultraviolet rays or radioactive materials, or as a secondary effect of intraocular or systemic diseases, such as diabetes, or from exposure to various drugs. Cataracts can be cortical, involving largely or exclusively changes in the outer portion of the lens, or dense nuclear, involving primarily changes deep in the interior of the lens, or can involve most if not all of the proteinaceous material of the lens.

Treatment for cataracts generally involves removal of all or part of the lens through a small surgical incision (generally of about 3 mm to about 9 mm in length) made in the limbus, the portion of the sclera adjacent the cornea. Typically the lens is replaced with a synthetic intraocular lens material, or a contact lens or a thick eyeglass is used to function as did the lens. Intracapsular cataract extraction ("ICCE") involves removal of the lens and the entire capsule. This technique is no longer in common use, except for subluxated lens and ocular trauma where the capsule or zonules are badly damaged. When extracapsular cataract extraction ("ECCE") is performed, a 4 to 7 mm portion of the anterior capsule and the nucleus of the lens are removed, leaving the posterior capsule behind.

The main thrust of more modern cataract surgery has been towards smaller limbal incisions and less invasive approaches. Indeed, the success of the newest techniques now being developed to preserve and restore accommodation (the ability to focus properly), such as refilling the entire lens with a synthetic substance once the cataractous material has been removed, will depend upon the development of new instruments that can remove cataractous materials, including cataractous nuclei, through the smallest possible hole made at the periphery of the lens capsule. It is an object of the present invention to provide such instruments.

SUMMARY OF THE INVENTION

The novel surgical cutting heads or tips of this invention comprise:

(1) A first, inner rotatable or oscillating head having a tapered or feather edge 360° around its distal tip, as well as at least one V notch to core the lens nucleus, and at least one curled wing to break and cut the aspirated material; and (2) A second, outer tube which is open at its distal end and disposed concentrically around the first tube so as to have an interior surface opposed to at least part of the exterior surface of the first tube to define a tolerance or gap between these tubes, to permit the inner tube to rotate relative to the outer tube without frictional engagement or binding.

The proximal end of the inner tube can be slightly recessed within the outer tube to provide the surgeon with greater control in cutting away only those portions of the lens that need to be removed and to prevent the lens from being caught by the sharp points of the cutting edge(s) of the distal end of the inner tube and being rotated or twisted when the inner tube is caused to rotate or oscillate. Also, advantageously, guards or overhanging portions can be provided on the proximal end of the outer tube to facilitate cutting and to substantially prevent pulling or twisting of the tissue being severed.

More particularly, the non-rotating tip of the outer tube has a bent tongue to prevent the aspirated material from rotating with the inner cutting head. The gap between the tongue and the distal end of the mobile inner tube is such that when the curled wing(s) pass beneath the fixed bent tongue, the moving curled blades or wings almost touch the fixed bent tongue, thus sheering the lens material trapped within the tip. The bent tongue serves also as an over hanging guard that prevents the posterior capsule from contacting the moving blade.

The so-called wings are further provided such that when the tip rotates in a clockwise direction, the lens material is cut by both the V notch or notches and the curled wing or wings. Moreover, the broken material inside the tip is propelled by the helicoidal or screw of archimedes action of the curled wings. This is the preferred mode of action for rapidly coring the central portion of the nucleus. In contrast, when the tip rotates in the counter-clockwise direction, the lens material is mainly cut by the V notches and the cutting action is less aggressive. This is the preferred mode of action when cutting close to the lens capsule.

The cutting heads or tips of the invention can replace cutting heads hitherto used in known surgical instruments of this general type. They provide significant advantages to the thus transformed instruments, among which is to fragment relatively large pieces of material to avoid blockages.

It is, therefore, an object of the invention to provide improved surgical cutting instruments.

A further object of the invention is to provide improved surgical cutting instruments, particularly for use in infusion/aspiration devices, for surgically removing cataractous tissue from the eye.

Other objects, features, and characteristics of the present invention as well as the methods of operation and functions of the related elements of structure, and the combination of parts and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

FIG. 1 (original) is a schematic perspective view of the surgical cutting head in accordance with a first embodiment of the invention;

FIG. 2 (original 9) is a schematic perspective view of a surgical cutting head in accordance with the invention showing a second embodiment thereof;

DETAILED DESCRIPTION OF THE PRESENTLY PREFERRED EXEMPLARY EMBODIMENTS

Figure 3:
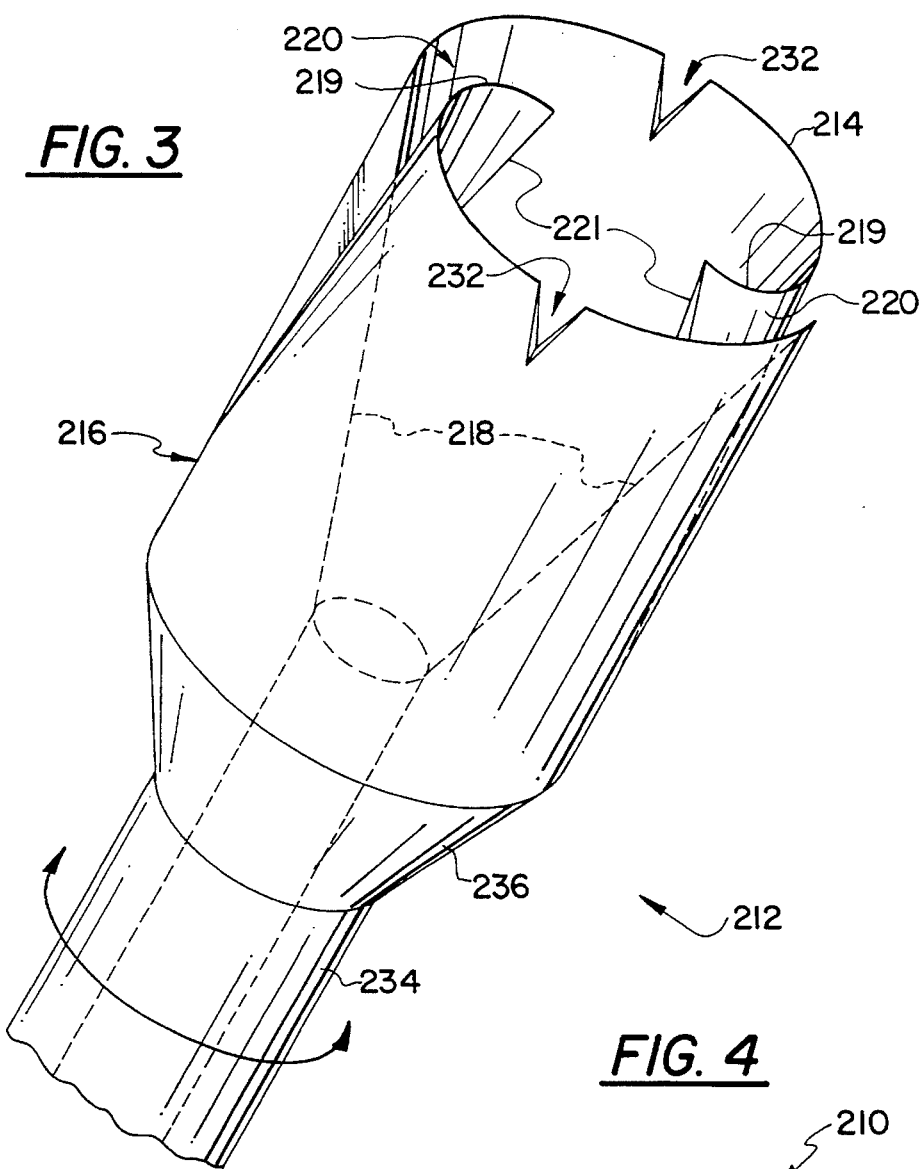
FIG. 3 (new) is a schematic perspective view of an inner tube or cutting head in accordance with a third and currently most preferred embodiment of the invention.

A surgical cutting head or tip 10 formed in accordance with a first embodiment of this invention is illustrated in FIG. 1 and certain aspects thereof were disclosed and claimed in our prior application Ser. No. 08/111,591, filed Aug. 25, 1993, and its parent application Ser. No. 07/913,474 filed Jul. 15, 1992, the disclosures of which are incorporated herein by this reference.

In the embodiment of FIG. 1, a first, inner tube 12 is provided for coring and cutting the material to be aspirated. Thus, the distal most tip of the inner tube has a sharp cutting edge 14. In the illustrated embodiment, the distal tip of the inner tube has a right cylindrical exterior surface 16 and an inclined inner surface 18 to define the cutting edge 14 at the distal most tip of the tube. It is to be appreciated, however, that a coring tip may be provided in another manner such as by bevelling both inner and outer surfaces of the tube, by providing only an inclined outer surface, by providing a scalloped end, etc.

The inner tube 12 also has at least one and preferably two curled wings 20 that are bent and curled inwardly of the inner tube 12. The curled wings 20 are adapted to break and cut the material cored by the cutting tip, for aspiration. In the illustrated embodiment, the curled wings are formed by axially cutting the inner tube to define an axial slit and then bending inwardly as a curled wing the material on one side of the slit. Furthermore, in the illustrated embodiment, each curled wing 20 is bent to extend inwardly for a distance of 20 to 30% of the diameter of the inner tube.

The inner tube 12 is mounted for rotation and/or oscillation in a known manner. Preferably, the assembly provided for rotating the inner tube (not shown) can selectively rotate it in a clockwise direction or in a counter clockwise direction depending upon the cutting action desired. In that regard, a clockwise rotation of the cutting inner tube will provide a more aggressive cutting action which, with the embodiment of FIG. 1, will primarily result in a coring cutting action. The oscillation of the tube is preferably transverse to the longitudinal axis of the inner tube, although not necessarily.

A known system (not shown) for infusing irrigating fluid and aspirating debris is operatively coupled to the proximal end of the cutting head assembly. Irrigating fluid is preferably delivered between the inner and outer tubes along a substantial portion of the length of the cutting tip and then the irrigation fluid is permitted to exit the instrument adjacent to but proximal of the distal tip, through radial irrigation fluid opening(s), as described more particularly below with reference to the embodiment of FIGS. 3–5. On the other hand, the aspiration suction is coupled to the interior passage of the inner tube 12 so as to remove the material cored and fragmented by the cutting tip. As an alternative, irrigation may be provided through another, separate instrument and only aspiration suction applied through the cutting tip of the invention.

The second, outer tube 22 is concentrically disposed around the inner tube. A gap 24 is defined between the inner and outer tubes to permit rotation of the inner tube 12 relative to the outer tube 22 without friction or binding. The gap 24 between the inner and the outer tube may be large enough for fluid passage. However, the gap 24 between inner and outer tubes at the distal most end is not a preferred fluid outlet.

The distal ends of the inner and outer tube may be co-terminus or the distal end of the inner tube may be slightly recessed within or project slightly beyond the exterior tube depending upon the material being cut by the inner tube and the presence of fragile structure(s) which are not to be cut. In the embodiment of FIG. 1, the outer tube 22 is provided at its distal end with at least one guard 26 which may include a portion 28 which overhangs the distal end of the inner tube 12 but is spaced therefrom. As can be appreciated, the guard 26 of FIG. 1 can provide several functions. First, it provides a structure forming a counter blade to prevent materials from being caught by the cutting tip and rotated with it. Also, the guard can limit tissue contact with the cutting blade to tissues that are drawn partially into the interior of the inner tube by aspiration, or protrude thereinto as a result of urging the cutting tip thereagainst.

The embodiment of FIG. 2 is similar to that of FIG. 1 except that the inner tube 112 projects significantly from the outer tube 122 when compared to the structure of FIG. 1. However, a portion of the outer tube is substantially co-terminus with the inner tube to define the over hanging guard 126 which, as noted above, provides for cooperation with the cutting edges of the inner tube 112, to permit a proper cutting action without undue rotation of the material being cut and removed.

Figure 4:
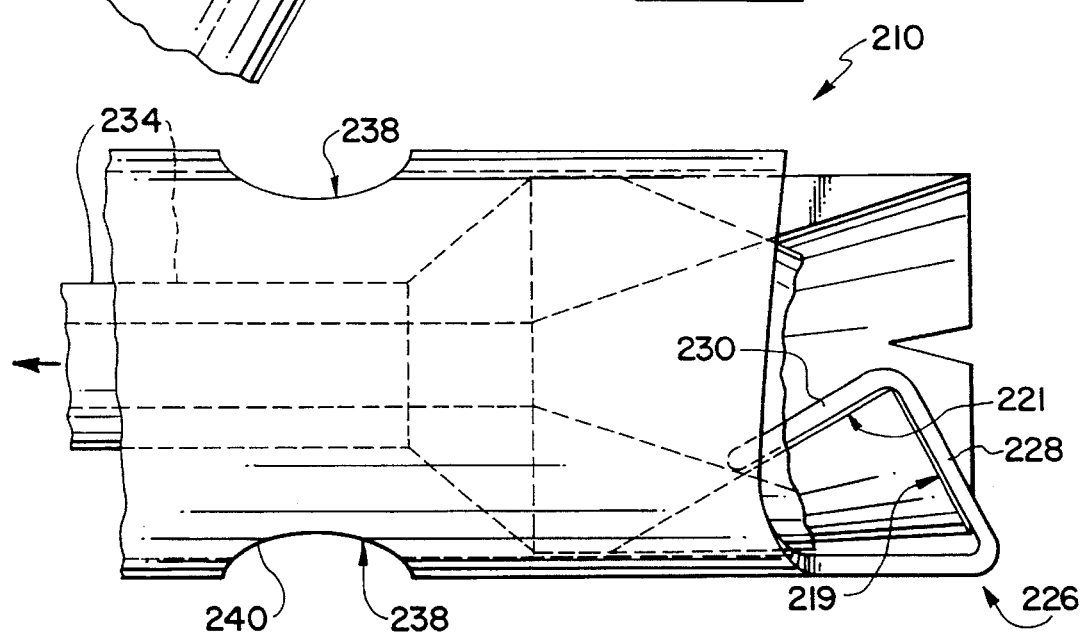
FIG. 4 is a schematic side elevational view of the cutting head of FIG. 3 within an outer tube in accordance with the invention.
Figure 5:
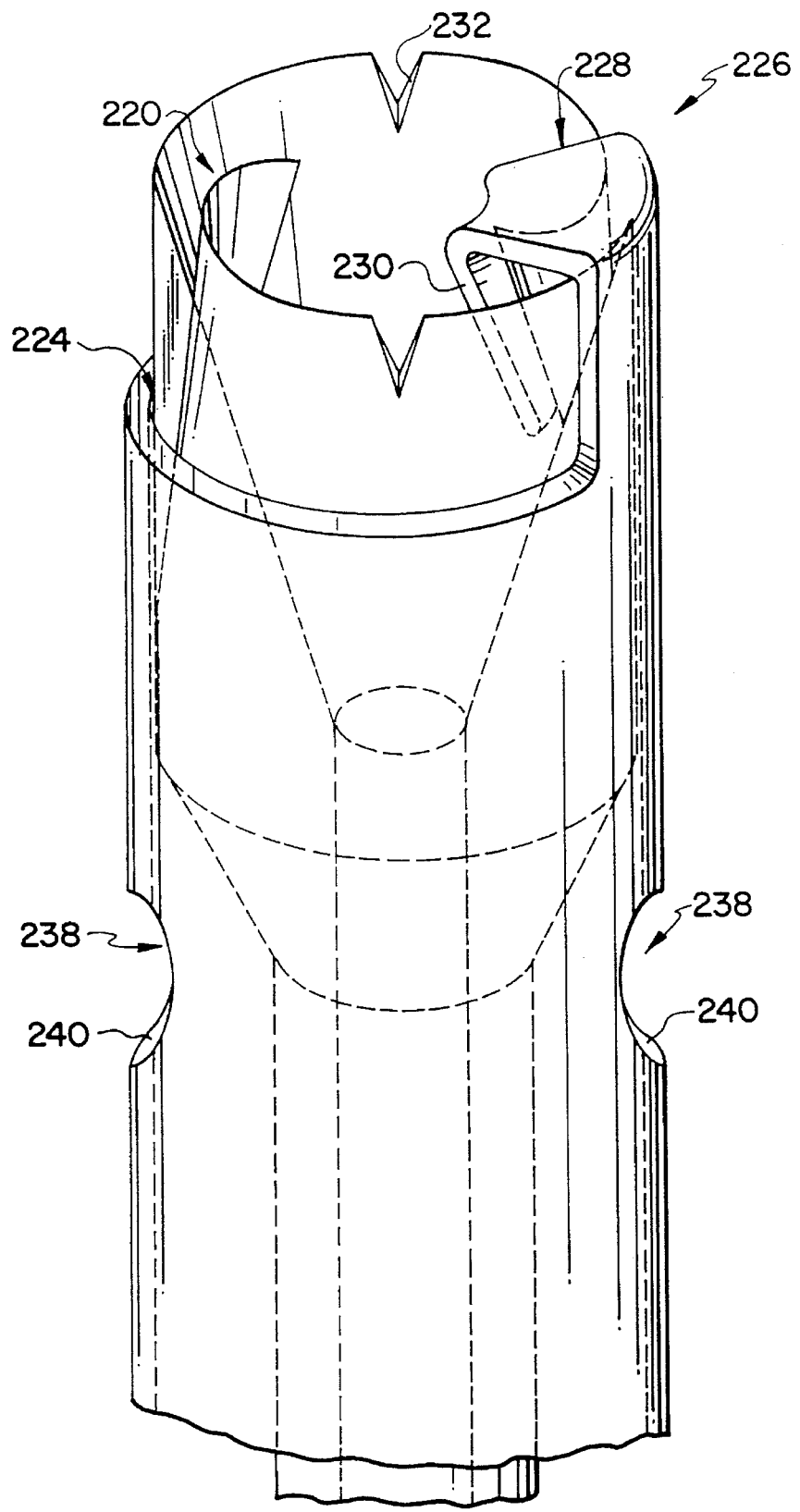
FIG. 5 is a schematic perspective view of the structure of FIG. 4.

The most preferred embodiment of the invention is illustrated in FIGS. 3–5. In addition to the curled wings 220, also provided in the embodiments of FIGS. 1 and 2, the embodiment of FIGS. 3–5 further includes first and second V notches 232 for supplementing the cutting action of the feather edge 214 and curled wings 220.

Although the inner tube 212 of the FIGS. 3–5 embodiment may be formed in any suitable manner, in the illustrated embodiment the inner tube is formed in two parts. The first part, defining the distal most tip, has a right cylindrical exterior surface 216 and a bevelled inner surface 218 to define the feather edge 214 and to define an inner passage having a gradually decreasing diameter, from the distal end proximally. The other part of the inner tube is in the form of a hollow tube or shaft 234 having an inner fluid and debris passage of substantially constant diameter. In the illustrated embodiment, to provide a gradual and smooth transition between the shaft and the cutting head, a silver-tin solder material 236 may be provided, or the tip may be otherwise machined or formed to define such a transition. Of course, the manner in which the inner tube is formed depends at least in part upon the material from which it is made.

With reference to FIGS. 4 and 5, it can be seen that the stationary outer tube 222 is of substantially constant inner and outer diameters. Thus, the necked down inner tube 212 naturally defines a passage 238 between the inner and outer tube through which irrigation fluid may flow. Irrigation port(s) 240 are defined in the outer tube adjacent the distal end of the irrigation passage.

In the embodiment of FIGS. 3–5, the protective guard 226 over hangs the inner tube 212 with a transverse portion 228 and an inwardly depending or bent tongue portion 230. This permits the guard to co-act with both the distal end edge 219 and inner curled edge 221 of the curled wing 220. The gap between the transverse and bent tongue portions of the guard 226 and the curled wings 220 is such that the two components almost touch. Thus, lens material trapped within the tip is sheared by the inter action of the curled wing and the protective guard 226.

By way of example, the overall length of surgical cutting heads 10, 110, 210 for cataract surgery made in accordance with this invention need be no longer than the maximum diameter of the cornea plus about 2 mm, hence about 15 mm. This length should allow the cutting head to reach the entire lens. Further, because of the increased efficiency which results from decreased blockages and frictional losses in these cutting heads while aspirating severed lens material, which in turn results from the ability of the cutting heads to further fragment relatively large pieces of such lens materials during aspiration, the diameter need be no greater than about 2 mm. For example, when practicing the standard extracapsular cataract extraction technique ("ECCE"), the cutting heads 10, 110, 210 can range from about 0.9 mm to about 2 mm in diameter. When practicing endocapsular cataract extraction techniques, involving lens refilling, or intercapsular cataract extraction, somewhat smaller holes or slits in the capsule can be made, e.g., holes ranging from about 0.9 mm to about 1 mm in diameter; hence in such cases the outer diameter of the outer tubes can be even smaller than about 2 mm. In all cases, of course, care will be taken when performing such surgical procedures to use a device sufficiently small in diameter so as not to unduly stretch the capsule wall through which the device is inserted.

The cutting heads 10, 110, 210 of this invention are preferably made of metal, such as stainless steel, particularly when such devices are constructed for use in performing cataract surgery. All or selected parts of these devices, the inner tube in particular, can also be made of materials such as ruby, sapphire, quartz, ceramics, or polyamide copolymers. By proper choice of the materials of construction, these devices can be made to be disposable in whole or in part, or reusable (after autoclaving or the use of ethylene oxide gas or other sterilization technique).

In use as a cataract surgical device, an infusion/aspiration device equipped with a cutting head 10, 110, 210 made in accordance with this invention, with irrigating fluid which can be introduced by any suitable means, e.g., from a mandrel containing "O" rings (not shown) through holes (not shown) in the outer tube flowing between the inner tube 12, 112, 212 and the outer tube 22, 122, 222 to infuse the eye, and with an aspirating vacuum of, e.g., from about 10 mm to about 700 mm Hg being applied through the inner space of the inner tube, will have its cutting head inserted by the ophthalmic surgeon into a previously made small, linear incision (usually about 1 mm to about 3 mm in length) in the limbus, with care being taken not to stretch the tissue. Because the lens is somewhat deformable, the aspirating vacuum applied through the cutting head draws the lens into contact with the distal end. The inner tube 12, 112, 212 set in motion by the surgeon, abrades the lens, to whatever extent desired, into small pieces.

These pieces of lens material are flushed from the surgical field and carried by the flowing irrigating fluid into the inner space of the inner tube under the influence of the aspirating vacuum. While passing through the inner space the pieces of lens material are further fragmented by the action of the cutting surface(s) of the curled wings, after which they pass from the inner tube with the flowing irrigating fluid for disposal.

A series of foot switches may be supplied, if desired, to allow the surgeon to control the flow of irrigating fluid, the aspiration force and the speed and direction of rotation or oscillation or the amount of vibration of the cutting head. A foot switch may also be used to occasionally cease aspiration and reverse the infusion of irrigating fluid. This permits the cutting head to be backflushed to dislodge the occasional large piece of aspirated lens material that might block the entrance of the cutting head, and also insures that the eyeball will not collapse during the procedure. If additional irrigation or steadying of the lens is necessary during a particular procedure, a separate "helper" handle can be used by the surgeon.

The above discussion of this invention is directed primarily to preferred embodiments and practices thereof. It will be readily apparent to those skilled in the art that further changes and modifications in the actual implementation of the concepts described herein can easily be made without departing from the spirit and scope of the invention as defined by the following claims.

We claim:

1. A surgical cutting instrument comprising:

(a) a first, hollow tube having a proximal end, a distal end, and a passage defined therebetween for transporting fluids and tissue particles therethrough, said distal end having a cutting edge, said first tube having at least one curled cutting wing for fragmenting tissue, said curled cutting wing being defined by a segment of a wall of said first tube that has been displaced inwardly relative to a remainder of said wall of said first tube, said curled cutting wing having at least one cutting edge, wherein said first tube has two generally V-shaped cutting notches defined in a distal end edge thereof, said cutting notches being diametrically opposed to one another, and (b) a second, hollow tube, having a proximal end, a distal end, and a passage defined therebetween, said second tube being disposed concentrically around said first tube and having at least one projecting guard defined at said distal end of said second tube and extending inwardly from a wall of said second tube so as to overlie at least a portion of said distal end of said first tube, said second tube having an exterior surface and an interior surface, said interior surface of said second tube being opposed to and spaced from an exterior surface of said first tube so as to permit rotation of said inner tube relative to said outer tube.

2. A surgical cutting instrument as in claim 1 wherein said first tube has two of said curled cutting wings.

3. A surgical cutting instrument as in claim 2, wherein said curled cutting wings are diametrically opposed to each other.

4. A surgical cutting instrument as in claim 1 wherein said curled cutting wing has a distal cutting edge and a longitudinal cutting edge.

5. A surgical cutting instrument as in claim 1 wherein each said curled cutting wing extends inwardly for a distance of between about 20 percent and about 30 percent of a distal end diameter of said first tube.

6. A surgical cutting instrument as in claim 1 further comprising a fluid passage defined between said first and second tubes and extending along at least a portion of the length of each of said tubes.

7. A surgical cutting instrument as in claim 6, further comprising at least one fluid outlet port defined through said wall of said second tube adjacent to but spaced from said distal end of said second tube.

8. A surgical cutting instrument comprising:

(a) a first hollow tube having a proximal end, a distal end, and a passage defined therebetween for transporting fluids and tissue particles therethrough, said distal end having a cutting edge, said first tube having two curled cutting wings for fragmenting tissue, each said curled cutting wing being defined by a segment of a wall of said first tube that has been displaced inwardly relative to a remainder of said wall of said first tube, each said curled cutting wing having at least one cutting edge, wherein said first tube has at least one generally V-shaped cutting notch defined in a distal end edge thereof, and (b) a second, hollow tube, having a proximal end, a distal end, and a passage defined therebetween, said second tube being disposed concentrically around said first tube and having at least one projecting guard defined at said distal end of said second tube and extending inwardly from a wall of said second tube so as to overlie at least a portion of said distal end of said first tube, said second tube having an exterior surface and an interior surface, said interior surface of said second tube being opposed to and spaced from an exterior surface of said first tube so as to permit rotation of said inner tube relative to said outer tube.

9. A surgical cutting instrument as in claim 8 wherein each said curled cutting wing extends inwardly for a distance of between about 20 percent and about 30 percent of a distal end diameter of said first tube.

10. A surgical cutting instrument as in claim 8 further comprising a fluid passage defined between said first and second tubes and extending along at least a portion of the length of each of said tubes.

11. A surgical cutting instrument comprising:

(a) a first, hollow tube having a proximal end, a distal end, and a passage defined therebetween for transporting fluids and tissue particles therethrough, said distal end having a cutting edge, said first tube having at least one curled cutting wing for fragmenting tissue, said curled cutting wing being defined by a segment of a wall of said first tube that has been displaced inwardly relative to a remainder of said wall of said first tube, said curled cutting wing having at least one cutting edge, and (b) a second, hollow tube, having a proximal end, a distal end, and a passage defined therebetween, said second tube being disposed concentrically around said first tube and having at least one projecting guard defined at said distal end of said second tube and extending inwardly from a wall of said second said first tube, said second tube having an exterior surface and an interior surface, said interior surface of said second tube being opposed to and spaced from an exterior surface of said first tube so as to permit rotation of said inner tube relative to said outer tube, wherein said projecting guard comprises a generally transverse portion which extends from said wall of said second tube inwardly to over hang said distal end of said first tube and a bent tongue portion which depends from said transverse portion so as to extend generally axially into said first tube.

12. A surgical cutting instrument as in claim 11, wherein said first tube has two of said curled cutting wings.

13. A surgical cutting instrument as in claim 12, wherein said curled cutting wings are diametrically opposed to each other.

14. A surgical cutting instrument as in claim 11 wherein each said curled cutting wing extends inwardly for a distance of between about 20 percent and about 30 percent of a distal end diameter of said first tube.

15. A surgical cutting instrument comprising:

(a) a first, hollow tube having a proximal end, a distal end, and a passage defined therebetween for transporting fluids and tissue particles therethrough, said distal end having a cutting edge, said first tube having at least one curled cutting wing for fragmenting tissue, said curled cutting wing being defined by a segment of a wall of said first tube that has been displaced inwardly relative to a remainder of said wall of said first tube, wherein said curled cutting wing has a distal cutting edge and a longitudinal cutting edge, and (b) a second, hollow tube, having a proximal end, a distal end, and a passage defined therebetween, said second tube being disposed concentrically around said first tube and having at least one projecting guard defined at said distal end of said second tube and extending inwardly from a wall of said second tube so as to overlie at last a portion of said distal end of said first tube, said second tube having an exterior surface and an interior surface, said interior surface of said second tube being opposed to and spaced from an exterior surface of said first tube so as to permit rotation of said inner tube relative to said outer tube, wherein said projecting guard comprises a first portion which extends from said wall of said second tube inwardly to selectively over lie said distal cutting edge of said curled cutting wing and a second portion which depends from said first portion so as to selectively over lie at least a portion of said longitudinal cutting edge of said curled cutting wing.

16. A surgical cutting instrument as in claim 15, wherein said first tube has two of said curled cutting wings.

17. A surgical cutting instrument as in claim 16, wherein said curled cutting wings are diametrically opposed to each other.

18. A surgical cutting instrument as in claim 15 wherein each said curled cutting wing extends inwardly for a distance of between about 20 percent and about 30 percent of a distal end diameter of said first tube.

* * * * *